United States Patent [19]
Cooke

[11] Patent Number: 5,279,578
[45] Date of Patent: Jan. 18, 1994

[54] MEDICAL NEEDLE WITH SHEATH AND FIXED HOLDER ENABLING SINGLE-HANDED USE

[76] Inventor: Thomas H. Cooke, 651 Strander Blvd., No. 100, Seattle, Wash. 98188

[21] Appl. No.: 921,378

[22] Filed: Jul. 30, 1992

Related U.S. Application Data

[63] Continuation of Ser. No. 663,749, Mar. 4, 1991, abandoned.

[51] Int. Cl.⁵ .................................................. A61M 5/32
[52] U.S. Cl. .................................... 604/192; 604/263; 206/365
[58] Field of Search ............... 604/192, 197, 198, 263; 206/363-

[56] References Cited

U.S. PATENT DOCUMENTS

| | | | |
|---|---|---|---|
| 4,485,918 | 12/1984 | Mayer | 604/263 |
| 4,610,667 | 9/1986 | Pedicano et al. | |
| 4,623,336 | 11/1986 | Pedicano et al. | |
| 4,737,149 | 4/1988 | Gillilan | 604/263 |
| 4,740,204 | 4/1988 | Masters et al. | |
| 4,799,927 | 1/1989 | Davis et al. | |
| 4,823,791 | 4/1989 | D'Amelio et al. | |
| 4,826,488 | 5/1989 | Nelson et al. | 604/192 |
| 4,846,803 | 7/1989 | Emerson | 604/192 |
| 4,852,844 | 8/1989 | Villaveces | |
| 4,880,413 | 11/1989 | Giuffre et al. | |
| 4,883,470 | 11/1989 | Haindl | |
| 4,892,525 | 1/1990 | Hermann, Jr. et al. | |
| 4,915,698 | 4/1990 | Levenson | 604/263 |
| 4,928,824 | 5/1990 | Barasch | |
| 4,938,354 | 7/1990 | Hernandez | 604/192 |
| 4,973,315 | 11/1990 | Sincock | 604/192 |
| 4,979,945 | 12/1990 | Wade et al. | 604/192 |
| 5,000,742 | 3/1991 | Morrison | 604/192 |
| 5,002,536 | 3/1991 | Thompson et al. | 604/192 |
| 5,021,049 | 6/1991 | Howard | 604/192 |
| 5,026,345 | 6/1991 | Teringo | 604/192 |
| 5,037,400 | 8/1991 | Curry | 206/365 |

FOREIGN PATENT DOCUMENTS 2617719  1/1989  France ........................ 604/263

Primary Examiner—John D. Yasko
Assistant Examiner—Ronald K. Stright, Jr.
Attorney, Agent, or Firm—Graybeal Jackson Haley & Johnson

[57] ABSTRACT

Means for safely handling medical needles such as needle electrodes, also known as surgical probes, and hypodermic needles. The needle handler can remove the needle for use and return the used needle to its sheath for disposal using only one hand, thereby avoiding any risk of inadvertent penetration of the used needle point in the other hand. The needle sheath is retained in fixed position in a stand or the like at the handler's work station and the sheath and stand are designed to render the sheathed needle readily installable in and removable from the stand by single-handed manipulation.

2 Claims, 3 Drawing Sheets

MEDICAL NEEDLE WITH SHEATH AND FIXED HOLDER ENABLING SINGLE-HANDED USE

This application is a continuation of application Ser. No. 07/663,749, filed Mar. 4, 1991 now adandoned.

BACKGROUND OF THE INVENTION

1. Field of the Invention

This invention relates to medical needles and means for handling same, and more particularly to medical needles such as electrosurgical probes or so-called electrical needle electrodes, and also hypodermic needles, and sheaths and holders therefor, especially adapted for single-handed use.

2. Description of the Prior Art

Medical needles such as hypodermic needles and needle electrodes, also called electrosurgical probes, are designed for and when properly used are disposable after one use, and as articles of commerce are supplied to the profession in sheaths or cases from which they are withdrawn for use, then returned to the sheath for disposal after use. Handling of the needle during use, particularly after the needle may have become contaminated by reason of the subcutaneous application of the needle to a patient, and particularly when the patient has a communicable disease such as AIDS, creates an undue risk of the medical person or other handler of the needle inadvertently handling the needle in such a manner that it pricks a finger or other body part of the handler, with the handler thereby contracting blood poisoning or the communicable disease. This risk occurs because, when reinserting the used needle into its sheath for disposal, the handler when holding the base of the needle in one hand and the sheath into which the needle is to be inserted in the other hand, can misgauge the entry of the needle tip into the opening in the sheath and the tip of the needle can pierce the finger or thumb or the handler holding the sheath. This problem has been recognized for some time, particularly in connection with the handling of hypodermic needles, and it is common practice to provide a flared, funnel-shaped guide opening for the needle sheath to aid the handler in moving the tip of the used needle into the sheath. Such arrangements are commonly called safety needle sheaths and typically are disclosed in:

| | |
|---|---|
| Pedicano et al | 4,610,667 |
| Pedicano et al | 4,623,336 |
| Masters et al | 4,740,204 |
| Davis et al | 4,799,927 |
| D'Amelio et al | 4,823,791 |
| Giuffre et al | 4,880,413 |
| Haindl | 4,883,470 |
| Hermann, Jr. et al | 4,892,525 |
| Barasch | 4,928,824 |

Safety needle sheaths with flared openings have partially solved the problem of inadvertent harmful handler contact with contaminated needles but the typical manner of manipulation of such still involves two-handed handling for reinsertion of the needle into the sheath, i.e. the holding of the needle or needle carrier in one hand and the holding of the sheath in the other.

SUMMARY OF THE INVENTION

A primary object and feature of the present invention is the provision of a disposable medical needle and sheath or case therefor which is usable in conjunction with a fixed position retainer such as a work place stand, the construction and arrangement of which enable a handler thereof to withdraw the needle from its sheath, apply it to the patient, remove it from the patient, and return the used needle to its sheath with only one hand, i.e. with single-handed manipulation, thus completely obviating the chance of inadvertent penetration of the used needle point in the other hand of the handler because the other hand need not be anywhere in the vicinity of the used needle.

It is also an object and feature of the needle and sheath of the present invention to provide a construction and arrangement of the needle and sheath components such that the needle is easily and simply assembled in a needle hub or handle and the needle and its hub are readily insertable in the sheath, the components of the assembly being of themselves relatively inexpensive and easily manufactured.

These and other objects, features and advantages of the invention will become apparent from the following description and accompanying drawings of certain preferred embodiments of the invention.

BRIEF DESCRIPTION OF THE DRAWINGS

FIG. 7 is a view of a less preferred but still usable stand in which a needle or sheath according to the present invention is frictionally retainable.

DESCRIPTION OF THE PREFERRED EMBODIMENT

Figure 1:
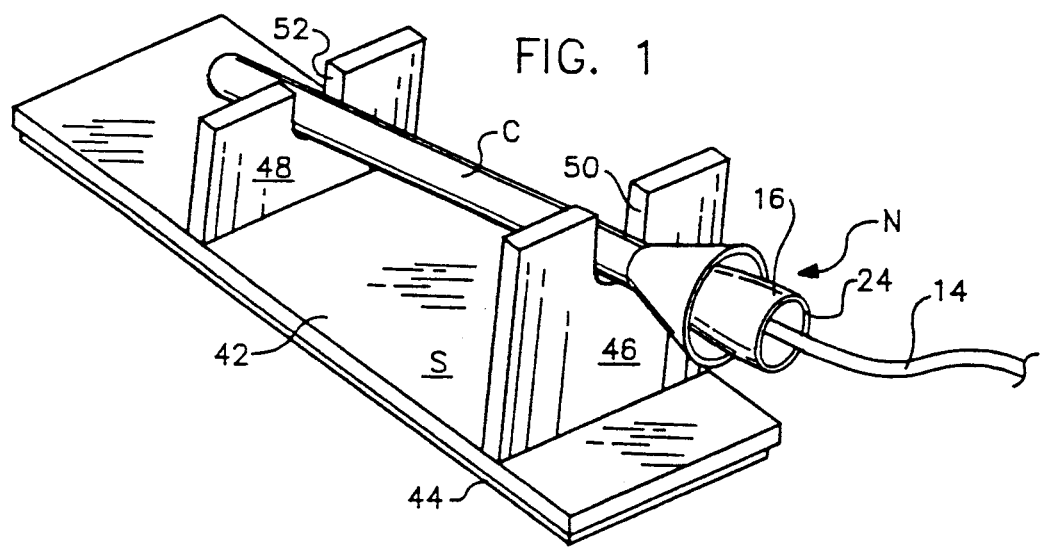
FIG. 1 is a perspective view of an assembled needle electrode and sheath according to the invention, along with a work place stand in which the sheath is supported and retained in a manner characteristic of the invention.

A typical and preferred embodiment of the needle/sheath/stand assembly according to the present invention is illustrated in FIGS. 1-6. Shown in perspective in FIG. 1 are the needle electrode N retained in its sheath or case C which is in turn releasably held in work place stand S.

The medical needle N selected for purposes of illustration is a needle electrode having a thin metal main body portion 10, and a ferrule portion 12 suitably of generally cylindrical form and of somewhat larger diameter than the main body portion 10, in which ferrule portion 12 connection is made from the needle main body 10 to an electrical wire lead 14. The needle electrode N further has a hub portion 16 formed of electrically nonconductive material such as molded semi-rigid plastic with an anchor sleeve 18 at one end having an inner diameter large enough to receive the needle main body 10 but smaller than an end cap 20 portion of ferrule 12, the hub portion 16 further having a bore 22 extending through the hub portion or handle 16 to the other end 24 thereof which bore is large enough adjacent the sleeve 18 to receive the end cap 20 and which is flared outwardly toward the other end 24 thereof to facilitate assembly of the needle main body 10, ferrule 12 and its cap 20 into the hub 16 as more fully described hereinafter.

Figure 2:
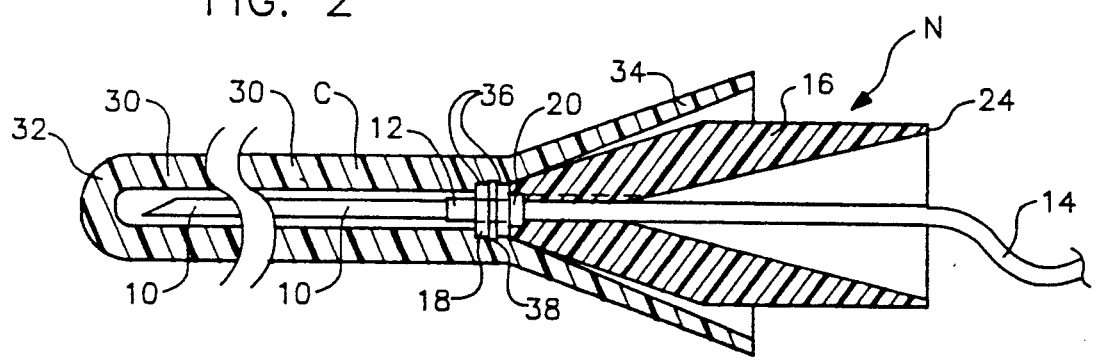
FIG. 2 is a cross-sectional view, partly in elevation and on an enlarged scale, taken along the longitudinal axis of the sheath and needle electrode shown in FIG. 1.
Figure 3:
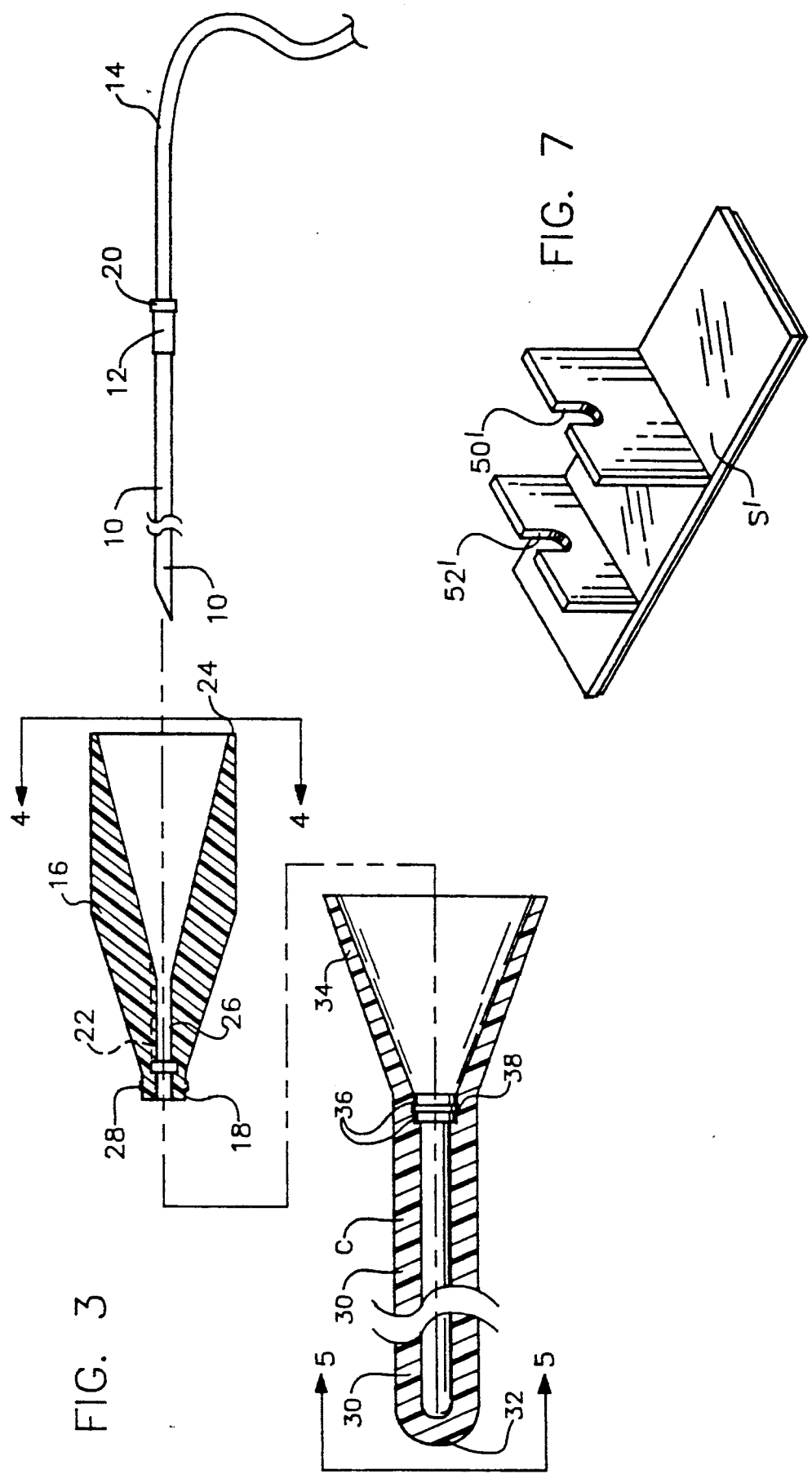
FIG. 3 is a view similar to that of FIG. 2, showing the components thereof in exploded view before assembly.
Figure 4:
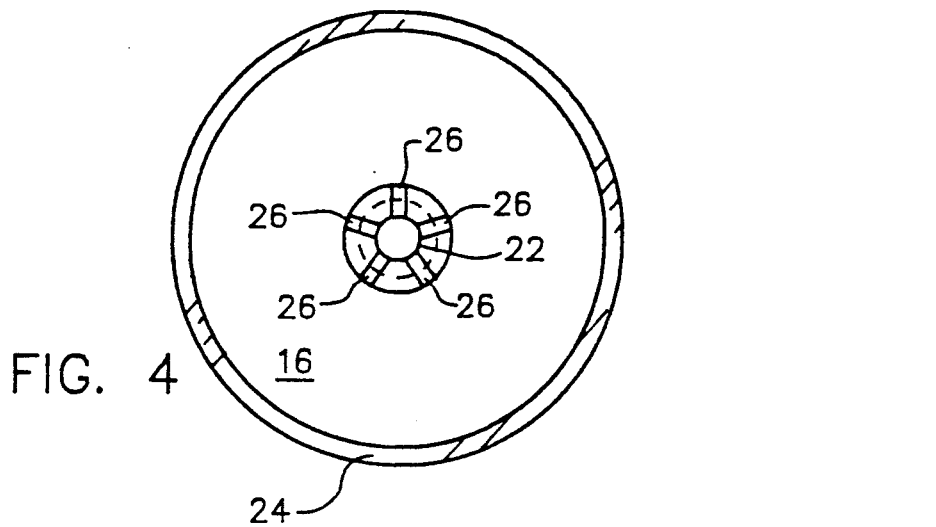
FIG. 4 is an end view of the hub portion of the needle electrode, taken substantially along line 4—4 of FIG. 3.
Figure 5:
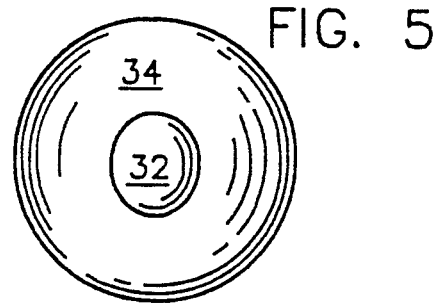
FIG. 5 is an end view of the sheath, taken substantially along line 5—5 of FIG. 3.

The hub inner bore 22 in its portion of lesser bore diameter comprises a plurality of radially and inwardly extending projection means in the form of fins or ribs 26 extending through a substantial portion of the hub, axially considered, and which terminate just short of the narrower bore portion of the bore 22, as shown in FIG. 3. The construction and configuration of the needle main body 10, ferrule portion 12, cap portion 20, bore 22 and fins 26 is such that assembly thereof as an article of commerce is facilitated. The outwardly flared end of the bore 22 facilitates initial introduction of the needle main body 10 into the hub portion 16. Then, as the needle components 10, 12, 20, 14 progressively enter the bore 22, the cap portion 20 engages the plastic fins 26, deforming them sufficiently to permit passage of the cap portion 20 therepast until the cap portion 20 seats against the sleeve 18 and the fins 26 return to the essentially radial position thereof and lock the seated cap portion 20 against the sleeve 18 as shown at FIG. 2, the needle electrode N thus being an integrated assembly.

It is shown in FIGS. 2 and 3, sheath C, also suitably fabricated of molded semi-rigid plastic, comprises a generally tubular main body 30 with a closed end 32 and an outwardly flared open end 34. Interiorly, between the main body 30 and flared open end 34, the sheath C has a short generally cylindrical bore 36 and annular groove 38 of a size to frictionally mate in sealing engagement with the needle's anchor sleeve portion 18 and raised rib 28 thereon with the needle N fully inserted in the sheath C (FIG. 2).

The sheath C and the needle electrode N with its hub portion or handle 16 are specifically configured for handling by medical personnel using only one hand. For such use the needle electrode N and its sheath C are used in conjunction with some means holding the sheath C in fixed position at the work place such as the stand S, shown in FIGS. 1 and 6, which comprises a base 42 attachable or otherwise anchorable to a work place fixed surface (not shown) such as a desk top, such attachment being suitably by an adhesive backing 44 or the like. The stand S also comprises front and rear upstanding panels 46, 48, each of which has a respective slot 50, 52 in which the main body portion 30 of the sheath C is received and retained. Thus the slots 50, 52 function as sheath receiving and retaining means. For this purpose, in the embodiments shown in FIGS. 1 and 6, the sheath C in lateral cross section in its main body portion 30 has an oblong, e.g. elliptical, form and the slots 50, 52 have a dimension between the walls thereof which is slightly larger than the minimum diameter of the sheath oblong cross section but slightly less than the maximum diameter thereof (which are respectively diagrammatically shown at 54, 56 in FIG. 6) so that the sheath C is simply retained in or readily released from engagement with the slots 50, 52 of stand S simply by slight axial rotation of the sheath C relative to the stand S. As will be readily evident, the handler of the sheathed needle electrode N can place the sheath C in the stand S with the sheath C in the orientation shown diagrammatically at 58 in FIG. 6. Then, while holding the sheath C and needle N with one hand with the thumb and the fingers grasping the hub portion 16 of the needle N and/or the flared portion 34 of sheath C and by axially rotating the sheath C slightly, as diagrammatical shown in FIG. 6 at arrow 62, the sheath C becomes wedged in the slots 50, 52 in substantially the position shown diagrammatically at 64 in FIG. 6. With the sheath C thus anchored in the stand S, the needle N can by axial withdrawal be removed from the sheath C by the user with the same hand, can be implanted in the patient, then on removal from the patient can be reinserted and frictionally re-engaged by full insertion of the needle N into the sheath C, whereupon with a reverse twist by the handler, axial rotation relieves the wedging of the sheath C in the slots 50, 52 and the resheathed needle may be withdrawn for discard, again with the handler using just one hand.

Figure 6:
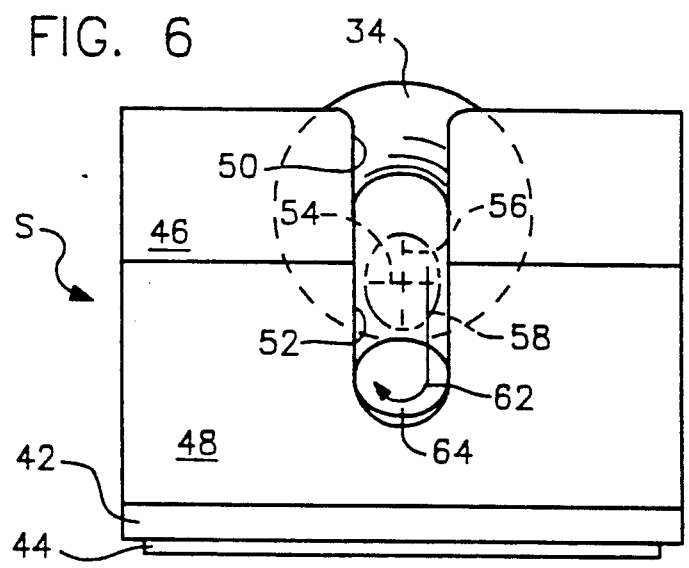
FIG. 6 is a rear end view of the sheath and stand illustrated in FIG. 1, diagrammatically showing one manner in which the sheath is lockable and releasable from the stand simply by an axial rotation of the sheath.

While the form of sheath C and stand S shown as at FIG. 6 are the presently preferred form for practice of the present invention, it will be apparent to those skilled in the art to which the invention is addressed that other means and arrangements can be employed for holding the needle sheath in a fixed or anchored position other than by the user holding it. Thus, as a less preferred form because it requires possibly more awkward or more cumbersome manipulation by the user, FIG. 7 illustrates a stand S' which can be otherwise like that shown in FIGS. 1 and 6, but which comprises slots 50' and 52' which have a dimension such as to frictionally fit and retain a needle sheath like sheath C except having a uniform cross-sectional diameter of a size to snugly fit the slots 50, 52'. Manipulation of the sheath to install it on the stand S' and remove it from the stand in such event can be simply by pressing the sheath downward into the slots and removal can be by simply pulling it upward or possibly pivotally moving it upwardly out of the slots against a pivotal contact of the closed end of the sheath with the base of the stand, i.e. by a prying movement.

While the description of the preferred embodiment and accompanying drawings are directed to the invention as applied to the construction and handling of a disposable needle electrode, it will be apparent that the features of the invention enabling a user to withdraw a medical needle from its sheath or case, use it, and return it to the sheath or case and dispose of it, all in a one handed manner, are equally applicable to hypodermic needles and the like.

The invention is not limited to the specific embodiments shown and discussed above and various modifications and adaptations thereof may be made within the scope of the accompanying claims without departing from the principles of the invention.

What is claimed is:

1. In the combination comprising:
   (1) a medical needle of a type to be disposed of after a single use,
   (2) An elongate sheath for said needle in which the needle is retained before and after use, said sheath having a closed end, a main body and an open end through which the needle is removable for use and insertable after use, and also having a hub portion extending slightly beyond the extent of the sheath when the needle is seated in the sheath so as to be readily graspable by the handler for withdrawal of the needle from the sheath and reinsertion of the needle into the sheath, (3) a sheath receiving stand at a fixed location at the handler's work station and in which the needle sheath is installable and removable in the course of use of the needle by the handler, the improvement wherein said sheath is characterized by a generally elliptical lateral cross section with its maximum diameter greater than its minimum diameter and said sheath receiving stand comprises at least one sheath receiving and retaining means laterally dimensioned to be slightly larger than the minimum diameter of the sheath cross section but less than the maximum diameter thereof, enabling the sheath to be rigidly retained in or readily released from the sheath receiving stand simply by the handler exerting a slight axial rotation of the sheath relative to the sheath receiving and retaining means, whereby the handler can insert the sheath containing the needle in the sheath receiving and retaining means, twist the sheath containing the needle to rigidly retain the sheath in the stand, withdraw the needle from the sheath and apply the needle to a patient then remove the same from the patient and reinsert the used needle in the sheath while the sheath continues to be rigidly retained in the stand, then reversely twist the sheath relative to the stand to release the needle and sheath from the stand, the handler all the while using but one hand to handle the needle and its sheath and thereby avoiding any risk of puncture by and contamination from the used needle.

2. In the combination of claim 1, the improvement wherein said sheath comprises a flared open end to facilitate insertion of the needle into the sheath.

* * * * *